United States Patent [19]

Shimizu et al.

[11] Patent Number: 4,572,800

[45] Date of Patent: Feb. 25, 1986

[54] HUMAN LEUKEMIA VIRUS-RELATED PEPTIDES, A PROCESS FOR PRODUCTION THEREOF, ANTIBODIES OF THE PEPTIDES AND A PROCESS FOR PRODUCTION OF THE ANTIBODIES

[75] Inventors: Fumio Shimizu; Tetsuya Tachikawa; Nobuhiro Ikei; Atunari Noda; Etsuro Hashimura; Kenichi Imagawa, all of Tokushima, Japan

[73] Assignee: Otsuka Pharmaceutical Co., Ltd., Tokyo, Japan

[21] Appl. No.: 535,118

[22] Filed: Sep. 23, 1983

[30] Foreign Application Priority Data

Sep. 30, 1982 [JP] Japan ............................... 57-171313
Feb. 16, 1983 [JP] Japan ............................... 58-25233

[51] Int. Cl.$^4$ .................. A61K 39/00; A61K 37/00; G01N 53/00; C07K 39/00
[52] U.S. Cl. ....................... 260/112.5 R; 260/112 R; 260/112 B; 514/15; 514/2; 514/6; 424/88; 424/85; 436/504; 436/544
[58] Field of Search ............ 260/112.5, 112 R, 112 B; 424/85, 88; 435/70; 436/501, 504, 512, 542, 544, 545, 64, 547

[56] References Cited

U.S. PATENT DOCUMENTS 4,298,593 11/1981 Ling .......................................... 424/1
4,407,965 10/1983 Yanaihara ............................. 436/547

OTHER PUBLICATIONS

Hopp et al. *Proc. Natl. Acad. Sci.* vol. 78(6) pp. 3824–3828 Jun. 1981 "Prediction of Protein Antigenic Determinants from Amino Acid Sequences".
Balacz et al. *Chemical Abstracts* V. 96(2) No. 11649b 1981 "Oligopeptide Selectively Inhibiting the Growth or Multiplication of Normal and Leukemic Myloid Cells, its Isolation from Healthy White Blood Cells or Granulucytes and Pharmaceuticals Containing the Peptide.
Levy et al. *Chem. Abstr.* V. 87 No. 13217Z 1977 "The in vitro Antibody Response to Cell Surface Antigens, I. The Henogenic Response to Human Leukemic Cells".
Seiki et al. *Proc. Nat'l. Acad. Sci.* V. 80 pp. 3618–3622 Jun. 1983 "Human Adult T-Cell Leukemia Virus: Complete Nucleotide Sequence of the Provirus Genome Integrated in Leukemia Cell DNA".
Guroff et al. *J. Exp. Med.* vol. 154 Dec. 1981 pp. 1957–1964 "Detection of the Human T Cell Lymphoma Virus P19 in Cells of some Patients with Cutaneous T Cell Lymphoma ... ".
Oroszlan et al. *Proc. Natl. Acad. Sci.* Feb. 1982 pp. 1291–1294 "Primary Structure Analysis of the Major Internal Protein P24 of Human Type C T-Cell Leukemia Virus".
Hinuma et al. *Proc. Natl. Acad. Sci.* vol. 78(10) Oct. 1981 pp. 6476–6480 "Adult T-Cell Leukemia: Antigen in an ATL Cell Line and Detection of Antibodies in the Antigen in Human Sera".
Kalyanarman et al. *Proc. Natl. Acad. Sci.* vol. 79, pp. 1653–1657 Mar. 1982 "Natural Antibodies to the Structural Core Protein (P27) of the Human T-Cell Leukemia ... in Japan".

(List continued on next page.)

*Primary Examiner*—Lionel M. Shapiro
*Assistant Examiner*—Robin Lyn Teskin
*Attorney, Agent, or Firm*—Sughrue, Mion, Zinn, Macpeak, and Seas

[57] ABSTRACT

An antibody of a human leukemia virus-related peptide obtained by collecting an antibody produced in a mammal body by administering to the mammal an antigen prepared by reacting a human leukemia virus-related peptide represented by formula (1):

R-Pro-Val-Met-His-Pro-His-Gly-Ala-Pro-OH     (1)

wherein
R is a hydrogen atom or a group shown by formula, H-Tyr-;
as a hapten, with a carrier in the presence of a hapten-carrier binding agent.

7 Claims, 2 Drawing Figures

OTHER PUBLICATIONS

Kalyanaraman et al. *Nature* vol. 29 Nov. 19, 1981 pp. 271-273 "Antibodies in Human Sera Reactive Against an Internal Structural Protein of Human T-Cell Lymphoma Virus".

Guroff et al. *Science* vol. 215 Feb. 19, 1982 pp. 975-978 "Natural Antibodies to Human Retro HTLV in a Cluster of Japanese Patients with Adult T Cell Leukemia".

Posner et al. *J. Exp. Med.* vol. 154 Aug. 1981 pp. 333-346 "Natural Antibodies to the Human T Cell Lymphoma Virus in Patients with Cutaneous T Cell Lymphomas".

Yoshida et al. *Proc. Natl. Acad. Sci.* vol. 79 Mar. 1982 pp. 2031-2035 "Isolation and Characterization of Retrovirus from Cell Lines of Human Adult T-Cell Leukemia and its Implication in the Disease".

Gotoh et al. *Proc. Natl. Acad. Sci.* Aug. 1982 pp. 4708-4782 "Healthy Carriers of a Human Retrovirus, Adult T Cell Leukemia Virus (ALTV): Demonstration by Clanal Culture . . . ".

Hinuma et al. *Int. J. Cancer* vol. 29 pp. 631-635 1982 "Antibodies to Adult T-Cell Leukemia Virus & Associated Antigen (ATLA) in Sera from Patients with ATL and Controls in Japan . . . ".

HUMAN LEUKEMIA VIRUS-RELATED PEPTIDES, A PROCESS FOR PRODUCTION THEREOF, ANTIBODIES OF THE PEPTIDES AND A PROCESS FOR PRODUCTION OF THE ANTIBODIES

BACKGROUND OF THE INVENTION

1. Field of the Invention

The present invention relates to a novel peptide associated with human leukemia virus (hereafter also referred to as ATLV short for adult T-cell leukemia virus or as HTLV short for human T-cell leukemia virus) and more particularly, to peptides associated with such viral infections as well as mature T-cell leukemia or lymphoma such as adult T-cell leukemia, cutaneous T-cell lymphoma, etc.

Further, the present invention relates to novel antibodies specific to the peptide.

The present invention also relates to processes for producing the antibodies.

2. Development of the Invention

In the specification, amino acids, peptides, protective groups, active groups, nucleotides and others are expressed pursuant to the IUPAC Rules, the IUB Rules or common symbols established in the art when they are abbreviated; examples of which are given below. In case that optical isomers can be present with respect to amino acids or the like, an L-form is meant unless otherwise indicated.

Pro: proline
Val: valine
Met: methionine
His: histidine
Gly: glycine
Ala: alanine
Tos: p-toluenesulfonyl group
Boc: tert-butoxycarbonyl group Human leukemia virus (ATLV or HTLV) is found in cultured media of T-cells from a patient with adult T-cell leukemia (hereafter referred to as ATL) and in cultured media of ATL cells established by mixed culture of T-cells from patient with ATL and normal T-cells, and therefore its association with the incidence of the disease is paid to a keen attention. Recently there have been reported several ATL-associated proteins specific to the virus or ATL (M. Yoshida et al: *Proc. Natl. Acad. Sci.*, U.S.A., vol. 79, 2031–2035, March (1982); S. Oroszlan et al: Ibid., vol. 79, 1291–1294, February (1982), and Symposium founding on Grant-in-Aid for Cancer Research from Ministry of Public Welfare "Adult T-cell Leukemia, Lymphoma (ATL) and Its Etiology", pp. 173–138 published by Life Science Center on Jan. 5, 1983.

As a result of extensive research aiming at development of a system which can be used for specifically measuring ATL-associated antigen (ATLA) and purification thereof, it is found that a certain peptide having an N-terminal peptide chain of p-24, which is known as one of antigenic proteins of ATLA, is useful as a hapten for p-24 and that antibodies prepared using this hapten are highly specific to ATLA.

The present invention has been accomplished based on the aforesaid findings and is directed to such ATL-associated antigen (ATLA) aiming at diagnosis of such virus infections as well as a process for preparation of and a method of measurement for a specific antibody to these peptides.

SUMMARY OF THE INVENTION

That is, the present invention provides an antibody of human leukemia virus-associated proteins obtained by collecting an antibody produced in a mammal body by administering to the mammal an antigen prepared by reacting a human leukemia virus-related peptide represented by general formula (I):

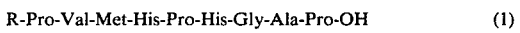

R-Pro-Val-Met-His-Pro-His-Gly-Ala-Pro-OH          (1)

wherein

R is a hydrogen atom or a group shown by general formula, H-Tyr-;

as a hapten, with a carrier in the presence of a hapten-carrier binding agent.

The present invention further provides a process for production of the foregoing antibody.

The present invention also provides human leukemia virus-related peptide and a process for production thereof.

DESCRIPTION OF THE PREFERRED EMBODIMENTS

Figure 1:
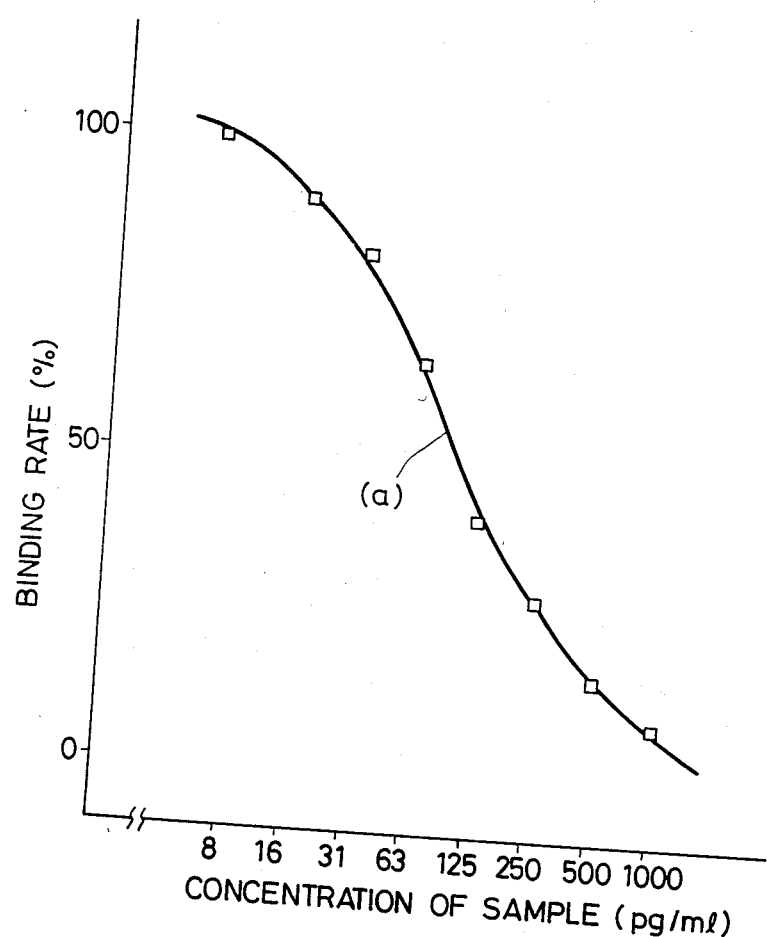
FIG. 1 is a curve showing the affinity of Peptide A to the antibody of the present invention.

The peptide of the present invention shown by formula (1) described above can all be easily prepared by simple operations utilizing easily accessible, commercially available amino acids. From the peptide, antigens can be prepared using them as a hapten. From the thus obtained antigens, antibodies having a specific reactivity with ATLA particularly with p-24 can readily be obtained in large amounts and stably. These specific antibodies are usable for purification of ATLA, by binding these antibodies to carriers for use of, e.g., affinity chromatography, and utilizing the bound antibodies in the chromatography, etc. The specific antibodies can also be utilized as specific antibodies in various immunological measurements of ATLA. Thus, these antibodies are useful for diagnosis of human leukemia virus infections and further for diagnosis, studies, etc. of mature T-cell leukemia or lymphoma such as adult T-cell leukemia, cutaneous T-cell lymphoma, etc. as well as diseases related thereto.

The peptide of the present invention represented by the general formula (1) can be prepared by conventional processes for synthesizing peptides; more specifically, using processes as described in Schroder and Luhke, *The Peptides*, vol. 1 (1966), published by Academic Press, New York, U.S.A., or Izumiya et al., *Synthesis of Peptides*, (1975), published by Maruzen Publishing Co., Ltd., for example, an azide process, a chloride process, an acid anhdride process, a mixed anhydride process, a DCC process, an active ester process (a p-nitrophenyl ester process, an N-hydroxysuccinimide ester process, a cyanomethyl ester process, etc.), a process using a Woodward reagent K, a carbodiimidazole process, an oxidative reduction process, a DCC/additive (HONB, HOBt, HOSu) process, etc. Solid phase and liquid phase syntheses are both applicable to the foregoing processes.

The peptides of the present invention are prepared in accordance with the aforesaid processes for synthesizing ordinary polypeptides, generally either by a so-called stepwise process which comprises condensing an amino acid to the terminal amino acid one by one in sequence, or by coupling fragments divided into several groups to the terminal amino acid. In more detail, for example, in case that a solid phase synthesis is adopted, the C terminal amino acid is bound to an insoluble carrier through its carboxyl group. The insoluble carrier is not particularly limited as long as it has a binding capability to a reactive carboxyl group. Examples of such insoluble carriers include halogenomethyl resins such as chloromethyl resin, bromomethyl resin, etc.; hydroxymethyl resins, phenol resins, tert-alkyloxycarbonylhydrazidated resins, etc.

After the amino protective group is removed, an amino group-protected amino acid is bound in sequence in accordance with the amino acid sequence shown by general formula (1) through condensation of its reactive amino group and the reactive carboxyl group, in sequence, to synthesize step by step. After synthesizing the complete sequence, the peptide is split off from the insoluble carrier to produce the protein.

In the foregoing process, it is preferred that histidine be protected at the side chain functional groups. These functional groups at the side chain are protected with ordinary protective groups which are split off after completion of the reaction. The functional groups which take part in the reaction are generally activated. These processes are known and reagents used in these processes are also appropriately chosen from known ones.

Examples of protective groups for amino groups include a benzyloxycarbonyl, Boc, tert-amyloxycarbonyl, isobornyloxycarbonyl, p-methoxybenzyloxycarbonyl, Cl-Z, adamantyloxycarbonyl, trifluoroacetyl, phthalyl, formyl, o-nitrophenylsulfenyl, diphenylphosphinothioyl group, etc.

Examples of protective groups for the imino group of histidine include a Tos, Bzl, benzyloxycarbonyl, trityl group, etc.

The hydroxy group of tyrosine can be protected by esterification with acetyl, benzoyl, etc. or by etherification with benzyl, tetrahydropyranyl. However, it is not always necessary to protect the hydroxy group of tyrosine.

Examples of activated carboxyl groups include the corresponding acid chlorides, acid anhydrides or mixed acid anhydrides, azides, active esters (esters with pentachlorophenol, p-nitrophenol, N-hydroxysuccinimide, N-hydroxybenzotriazole, N-hydroxy-5-norbornene-2,3-dicarboxydiimide, etc.)

In some cases, the peptide bond forming reaction may also be carried out in the presence of carbodiimide reagents such as dicyclohexylcarbodiimide, carbodiimidazole, etc. or tetraethylpyrophosphine, etc.

Hereafter, the preparation of the peptide in accordance with the present invention will be explained more specifically with reference to reaction equations below, as an example.

(Reaction Equation 1)

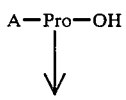
(a)

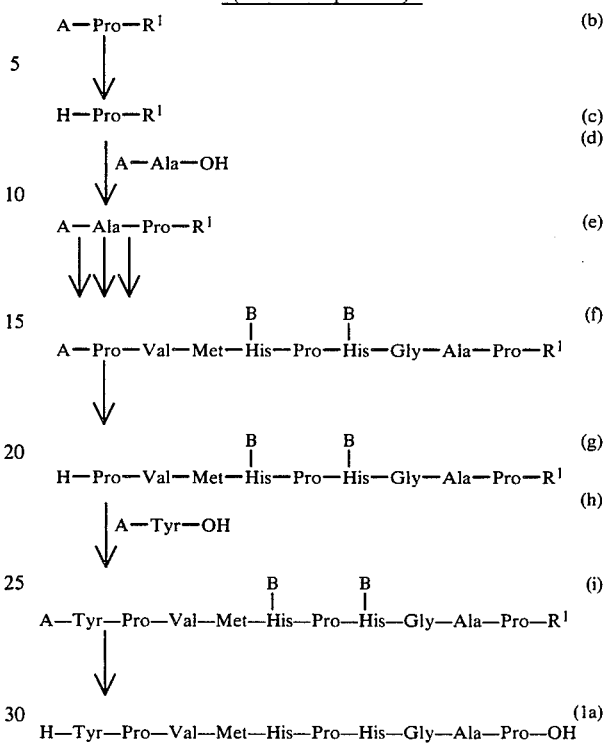

wherein A represents a protective group for an amino group, B represents a protective group for an imino group of histidine, and $R^1$ represents an insoluble carrier.

Of the foregoing, preferred examples of A include Boc, a benzyloxycarbonyl group, a p-methoxybenzyloxycarbonyl group or the like, preferred examples of B include Tos and the like and preferred examples of $R^1$ include chloromethylated polystyrene, hydroxymethylpolystyrene or the like, respectively.

In case that amino acids used possess functional groups at the side chain thereof which do not participate in each of the reactions, the amino acids are protected by the protective groups described above in a conventional manner and the protective groups are split off at the same time as splitting-off of the insoluble carrier $R^1$.

In the processes described above, the reaction of the amino acid (a) with the insoluble carrier $R^1$ is carried out by utilizing the reactive carboxyl group of the amino acid (a) and binding it to $R^1$ in a conventional manner. The reaction is effected in an appropriate solvent in the presence of basic compounds, e.g., triethylamine, potassium tert-butoxide, cesium carbonate, cesium hydroxide, etc. Examples of solvents include dimethylformamide (DMF), dimethylsulfoxide (DMSO), pyridine, chloroform, dioxane, dichloromethane, tetrahydrofuran, N-methylpyrrolidone, hexamethylphosphoric acid triamide, etc. or a mixture solvent thereof. The above reaction is generally completed at temperatures of about 0° to about 85° C., preferably at 25° to 80° C. for several minutes to about 24 hours. It is preferred that an amount of the amino acid to the insoluble carrier be set forth such that the former is employed in an excess amount, generally 1 to 3 time equivalents per equivalent of the latter.

Splitting of the protective group A for the thus obtained amino acid in a solid phase shown by general formula (b) is carried out in a conventional manner. For example, there are hydrogenation using catalysts such as palladium, palladium black, etc.; a reductive method such as reduction with metallic sodium in liquid ammonia; acidolysis using strong acids such as trifluoroacetic acid, hydrogen chloride, hydrogen fluoride, methanesulfonic acid, hydrogen bromide, etc. The hydrogenation using the foregoing catalysts can be carried out, e.g., under hydrogen pressure of 1 atm at temperatures of 0° to 40° C. It is preferred that the catalyst be used generally in an amount of about 100 mg to about 1 g. The reaction is generally completed within about 1 to about 48 hours. The acidolysis described above is carried out generally at temperatures of about 0° to about 30° C., preferably 0° to 20° C. for about 15 minutes to about 1 hour, in the absence of any solvent. It is preferred that the acid be used in an amount of generally 5 to 10 times that of the raw compound. When splitting-off of the protective group A alone is desired in the acidolysis, it is preferred to use trifluoroacetic acid or hydrogen chloride as the acid. The aforesaid reduction with metallic sodium in liquid ammonia can be carried out generally at temperatures of about −40° to about −70° C., using metallic sodium in such an amount that the reaction mixture is colored to permanent blue for about 30 seconds to about 10 minutes.

The reaction of the subsequently obtained amino acid in a solid phase shown by general formula (c) and the amino acid (d) (or a derivative thereof in which the carboxyl group is activated) is carried out in the presence of a solvent. As solvents, there can be used various known solvents conventionally used in peptide condensation, for example, anhydrous dimethylformamide, dimethylsulfoxide, pyridine, chloroform, dioxane, dichloromethane, tetrahydrofuran, ethyl acetate, N-methylpyrrolidone, hexamethylphosphoric acid triamide or a solvent mixture thereof. The reaction can also be conducted, if necessary and desired, in the presence of reagents conventionally employed in ordinary peptide bond forming reactions, for example, dehydrating and condensing agents such as carbodiimides, e.g., N,N-dicylohexylcarbodiimide (DCC), N-ethyl-N'-dimethylaminocarbodiimide, 1-ethyl-3-diisopropylaminocarbodiimide, 1-cyclohexyl-3-(2-morpholinyl-4-ethyl)carbodiimide, etc. While there is no particular limitation to the proportion of the amino acid (c) to the amino acid (d) to be used, it is preferred that the latter be employed in an amount of an equimolar amount to 10 time moles that of the former, preferably from an equimolar amount to 5 time moles. There is no particular limitation to the amount of the dehydrating and condensing agent to be used, either; the agent is generally employed preferably in an equimolar amount to that of the amino acid (d). The reaction temperature is suitably chosen from a normal range conventionally used for peptide bond forming reactions, generally from the range of about 0° C. to about 60° C., preferably from the range of about 0° C. to about 40° C. The reaction time is generally set forth for about several minutes to about 30 hours.

The thus obtained peptide shown by general formula (e) is, after splitting-off the protective group A as described above, condensed in sequence with each of the amino acids, A-Gly-OH,

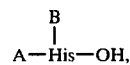

A-Pro-H,

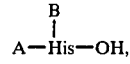

A-Met-OH, A-Val-OH, A-Pro-OH and A-Tyr-OH in accordance with the amino acid sequence shown by general formula (1) or, derivatives thereof wherein the functional groups at the side chain are protected or the carboxyl groups are activated. Thus, the peptide shown by general formula (e) can be introduced into the peptide represented by general formula (i). These condensation and splitting-off of the protective group A are carried out in a manner similar to those described above.

The thus obtained peptide (i) can be introduced into the peptide shown by general formula (1a) corresponding to the peptide shown by general formula (1) in which R represents a hydrogen atom by splitting-off of the protective group A, splitting-off of the protective groups of the amino acid at the side chain thereof and removing the insoluble carrier $R^1$. Here the removal of the protective group B and of the insoluble carrier $R^1$ can be carried out in a manner similar to the splitting-off of the protective group A; in this case, it is preferred to use hydrogen fluoride or hydrogen bromide as the acid. The peptide of the general formula (1) in which R represents a hydrogen atom can be obtained from the peptide of the general formula (g) by splitting the protective group B and insoluble carrier $R^1$ in a manner similar to the aforesaid splitting. All of the amino acids used in the aforesaid processes may be those commercially available.

The thus produced peptide of the present invention shown by formula (1) can be isolated and purified from the reaction mixture by means of peptide separation, e.g., extraction, distribution, column chromatography, etc.

The thus obtained peptides of the present invention are utilizable as labelled antigens employed in radioimmunoassay (RIA) or enzyme immunoassay (EIA), by introducing thereto radioactive substances such as $^{125}$I, $^{131}$I, etc.; various enzyme reagents such as peroxidase (POX), chymotripsinogen, procarboxypeptidase, glyceraldehyde-3-phosphatedehydrogenase, amylase, phosphorylase, D-Nase, P-Nase, β-galactosidase, glucose-6-phosphate dehydrogenase, ornithine decarboxylase, etc. The introduction of the above radioactive substance can be effected in a conventional manner. For example, the introduction of radioactive iodine can be carried out by the oxidative iodination method using chloramine T (W. M. Hunter and F. C. Greenwood, Nature, 194, 495 (1962), Biochem. J., 89, 144 (1963)), etc.

More particularly, this method can be carried out in an appropriate solvent, e.g., 0.2M phosphate buffer solution (pH 7.4) in the presence of chloramin T at about room temperature for about 10 to 30 seconds. The peptide, radioactive iodine and chloramine T are used in ratios of about 1 mCi of the radioactive iodine per nmol of tyrosine contained in the peptide and 10 to 100 nmol of chloramin T per nmol of tyrosine contained in the peptide when introducing one atom of the radioactive iodine per molecule of tyrosine, and about 2 mCi of the radioactive iodine per nmol of tyrosine contained in the peptide and 10 to 100 nmol of chloramin T per nmol of tyrosine contained in the peptide when introducing two atoms of the radioactive iodine per molecule of tyrosine. The thus prepared radioactive iodine labelled peptides can be isolated and purified from the reaction mixture by a conventional separation techniques, e.g., extraction, distribution, column chromatography, dialysis, etc. The thus obtained peptides can be stored after freeze drying, if desired.

The introduction of enzyme reagents can be conducted by known methods such as conventional coupling reactions, e.g., the B. F. Erlanger, et al method (*Acta Endocrinol. Suppl.*, 168, 206 (1972)), the M. H. Karol et al method (*Proc. Natl. Acd. Sci. U.S.A.*, 57, 713 (1967)), etc. That is, a peptide and an enzyme are reacted in a buffer solution having a pH of 4 to 6, e.g., 1 mM acetate buffer (pH 4.4) in the presence of an oxidizing agent such as $NaIO_4$ at about room temperature for 2 to 5 hours, followed by reduction with $NaBH_4$ or the like. The enzyme can be used in an amount of 1 to 3 mols per mol of the peptide. It is preferred that the oxidizing agent be used in an amount of about 100 to about 300 mols per mol of the peptide and the reducing agent be used in an amount of about 1 to about 2 mols per mol of th oxidizing agent. The thus obtained enzyme-labelled peptide can be isolated, purified and stored in a manner similar to the processes used in the case of the radioactive iodine-labelled peptide.

Hereafter processes for production of antigens using the peptides of the present invention as haptens will be described in detail.

The aforesaid antigens are prepared by using the peptides of the present invention as haptens and reacting the peptides with a suitable carrier in the presence of a hapten-carrier binding agent. In this case, natural and synthetic proteins having a high molecular weight which are conventionally employed in the preparation of antigens can be widely employed as carriers to be bound to haptens. Examples of such carriers include albumins of animal sera such as horse serum albumin, bovine serum albumin, rabbit serum albumin, human serum albumin, sheep serum albumin, etc.; globulins of animal sera such as horse serum globulin, bovine serum globulin, rabbit serum globulin, human serum globulin, sheep serum globulin, etc.; thyroglobulins of animals such as horse thryoglobulin, bovine thyroglobulin, rabbit thyroglobulin, human thyroglobulin, sheep thyroglobulin, etc.; hemoglobulins of animals such as horse hemoglobulin, bovine hemoglobulin, rabbit hemoglobulin, human hemoglobulin, sheep hemoglobulin, etc.; hemocyanins of animals such as Keyhole limpet hemocyanin (KLH), etc.; proteins extracted from ascaris (ascaris extracts, those described in Japanese Patent Application (OPI) No. 16414/81, *J. Immun.*, 111, 260–268 (1973), ibid., 122, 302–308 (1979), ibid., 98, 893–900 (1967) and *Am. J. Physiol.*, 199, 575–578 (1960), or purified products thereof); polylysine, polyglutamic acid, lysine-glutamic acid coplymers, copolymers containing lysine or ornithine, etc.

As hapten-carrier binding agents, those conventionally employed in the preparation of antigens can be widely employed. Specific examples of these agents include diazonium compounds for cross linking tyrosine, histidine, tryptophane, etc., e.g., bisdiazotized benzidine (BDB), bisdiazotized-3,3'-dianisidine (BDD), etc.; aliphatic dialdehydes for cross linking an amino group with an amino group, e.g., glyoxal, malonedialdehyde, glutaraldehyde, succinaldehyde, adipaldehyde, etc.; dimaleimide compounds for cross linking a thiol group with a thiol group, e.g., N,N'-o-phenylenedimaleimide, N,N'-m-phenylenedimaleimide, etc.; maleimidocarboxyl-N-hydroxysuccinimide esters for cross linking an amino group with a thiol group, e.g., metamaleimidobenzoyl-N-hydroxysuccinimide ester, 4-(maleimidomethyl)-cyclohexane-1-carboxyl-N'-hydroxysuccinimide ester, etc.; agents used in conventional peptide bond forming reactions in which amide bonds are found from an amino group and a carboxyl group, e.g., dehydrating and condensing agents such as carbodiimides, e.g., N,N-dicylohexylcarbodiimide, N-ethyl-N'-dimethylaminocarbodiimide, 1-ethyl-3-diisopropylaminocarbodiimide, 1-cyclohexyl-3-(2-morpholinyl-4-ethyl)carbodiimide, etc. As the foregoing hapten-carrier binding agent, it is also possible to use diazonium aryl carboxylic acids such as p-diazonium phenylacetic acid, etc. with conventional peptide bond forming agents such as the dehydrating and condensing agents described above in combination.

The reaction for preparing the antigens described above is carried out in an aqueous solution or a conventional buffer solution having pH of 7 to 10, preferably in a buffer solution having pH of 8 to 9, at temperatures of about 0° to 40° C., preferably around room temperature. The reaction is generally completed within about 1 to about 24 hours, preferably 3 to 5 hours. Representative examples of buffer solutions which can be used in the above process include:

0.2M sodium hydroxide-0.2M boric acid-0.2M potassium chloride buffer solution 0.2M sodium carbonate-0.2M boric acid-0.2M potassium chloride buffer solution 0.05M sodium tetraborate-0.2M boric acid-0.05M sodium chloride buffer solution 0.1M dihydrogen potassium phosphate-0.05M sodium tetraborate buffer solution In the above, proportions of the hapten, hapten-carrier binding agent and carrier can be appropriately determined but it is preferred that the carrier be employed in an amount of about 1 to about 6 times, preferably about 1 to about 5 times the weight of the hapten and the hapten-carrier binding agent be employed in an amount of about 5 to about 10 times the mol of the hapten. By the above reaction, the carrier is bound to the hapten via the hapten-carrier binding agent to obtain a desired antigen composed of a peptide-carrier complex.

After completion of the reaction, the thus obtained antigen can easily be isolated and purified by means of a dialysis method, a gel filtration method, a fractionation precipitation method, etc.

The thus obtained antigen binds 5 to 60 mols in average of the peptide thereto per mole of a protein and enables one to subsequently prepare an antibody having a high specificity to the antigen. Particularly, antigens to which the peptide is bound in an amount of 5 to 20 mols, preferably 8 to 15 mols, in average, per mole of a protein are preferred since they have higher specificity and enable one to obtain antibodies having high activity and sensitivity.

The preparation of an antibody using the antigen is carried out by administering the aforesaid antigen to mammals to thereby produce a desired antibody in vivo and collecting the antibody.

While there is no particular limitation to mammals provided for the preparation of antibodies, it is generally preferred to use rabbits or guinea pigs. In the production of antibodies, a definite amount of the antigen obtained as described above is diluted with a physiological saline solution to a suitable concentration and the resulting dilution is mixed with a complete Freund's adjuvant to prepare a suspension. The suspension is administered to mammals. For example, the aforesaid suspension is intracutaneously administered (0.1 to 5 mg/time as the amount of the antigen) to rabbit. Then the suspension is administered every two weeks over a period of 2 to 10 months, preferably 4 to 6 months to effect immunization. The collection of the antibody is carried out by collecting blood from the immunized animal after the passage of 1 to 2 weeks subsequent to the final administration, centrifuging the blood and isolating serum from the blood. According to this procedure, an antibody having an excellent specificity to the antigen used, especially p-24, can be collected and used for assaying human leukemia virus-related proteins utilizing RIA, EIA, etc.

The antibodies of the present invention can be labelled with enzymes or fluorescent substances conventionally used and can be used in EIA, fluorescence immunoassay (FIA), etc. Further, the antibodies of the present invention can be insolubilized by reacting them with a conventional solubilizing agent.

For purposes of explaining the present invention in more detail, preparations of the peptides shown by general formula (1), antigens obtained from the peptides and antibodies will be shown by way of examples but the present invention is not deemed to be limited thereto.

Rf values in the respective preparation examples were measured using solvent mixtures described below by means of thin layer chromatography on silica gel.

$Rf^1$ ... n-butanol-acetic acid-water (4:1:5)
$Rf^2$ ... n-butanol-acetic acid-pyridine-water (15:3:10:12)

Preparation of Peptides

SYNTHESIS EXAMPLE 1

(1) In 14 ml of a DMSO solution of 5.88 milliequivalents of potassium tert-butoxide 1.42 g of a Boc-Pro-OH was dissolved and 5 g of chloromethylated polystyrene resin (Protein Research Promotion Foundation) was added to the solution. The mixture was reacted at 80° C. for 30 minutes. After thoroughly washing the resin sequentially with DMSO, 50% acetic acid/chloroform and methylene chloride, the resin was dried under reduced pressure to obtain 5.27 g of Boc-Pro-resin.

A part of the Boc-Pro-resin was hydrolyzed and subjected to amino acid analysis. The results indicate that the product contained 0.36 mmol of the amino acid/g of the resin.

(2) After washing 4 g of the Boc-Pro-resin obtained in (1) above three times with 30 ml of chloroform, the resin was added to 30 ml of a chloroform solution of 50% trifluoroacetic acid (TFA) and the mixture was reacted at room temperature for 20 minutes. The reaction mixture was washed once with 30 ml of chloroform, 5 times with 30 ml of methylene chloride, 3 times with 30 ml of a methylene chloride solution of 10% triethyl amine and then 6 times with 30 ml of methylene chloride to obtain H-Pro-resin.

To 25 ml of a solution of 0.68 g of Boc-Ala-OH in methylene chloride the H-Pro-resin described above was added and 5 ml of a solution of 0.74 g of DCC in methylene chloride was then added to the resulting mixture. The mixture was reacted at room temperature for 2 hours. After washing the resin 6 times with 30 ml of methylene chloride, the resin was added to 25 ml of a methylene chloride solution of 0.68 g of Boc-Ala-OH and 0.55 g of 1-hydroxybenzotriazole. Then, 5 ml of a methylene chloride solution of 0.74 g of DCC was added thereto and the resulting mixture was again reacted in a similar manner (double coupling). The resin was thoroughly washed with methylene chloride to obtain Boc-Ala-Pro-resin.

(3) In a manner similar to (2) described above, des-tert-butoxycarbonylation (hereafter simply referred to as des-Boc) of the Boc-Ala-Pro-resin was conducted and amino acids described below were then condensed in order, each followed by conducting des-Boc.

| | |
|---|---|
| Boc—Gly—OH | 0.63 g |
| Boc—His—OH<br>\|<br>Tos | 1.47 g |
| Boc—Pro—OH | 0.77 g |
| Boc—His—OH<br>\|<br>Tos | 1.47 g |
| Boc—Met—OH | 0.90 g |
| Boc—Val—OH | 0.78 g |
| Boc—Pro—OH | 0.77 g |

Thus 2.2 g of H-Pro-Val-Met-His(Tos)-Pro-His(Tos)-Gly-Ala-Pro-resin was obtained. To the thus obtained resin 2 ml of anisole, 25 ml of hydrogen fluoride and 0.5 ml of ethanedithiol were added. After reacting the mixture at −20° C. for 30 minutes and then at 0° C. for 30 minutes, a peptide was obtained. Purification of the peptide using Sephadex G-25 (manufactured by Pharmacia Co., Ltd.; eluting liquid, 10% aqueous acetic acid solution), CM-Sephadex C-25 (manufactured by Pharmacia Co., Ltd.; eluting liquid, 0.1–0.5M aqueous ammonium acetate solution; concentration gradient, pH=4) and then HPLC (eluting liquid, 0.01% aqueous ammonium acetate solution:acetonitrile-=70:30) using μ-Pondapack C-18 (manufactured by Waters Co., Ltd.) gave 341 mg of H-Pro-Val-Met-His-Pro-His-Gly-Ala-Pro-OH (hereafter referred to as "Peptide A").

Rf values: $Rf^1=0.03$; $Rf^2=0.27$.

Elemental Analysis: (as H-Pro-Val-Met-His-Pro-His-Gly-Ala-Pro-OH. $CH_3CO_2H.5H_2O$):

| | C (%) | H (%) | N (%) |
|---|---|---|---|
| Calcd. | 48.38 | 7.11 | 16.67 |
| Found | 48.12 | 7.28 | 16.39 |

Amino Acid Analysis (analyzed with Hitachi 835 Model):

| Amino Acid | Analytical Data |
|---|---|
| Gly (1) | 1.04 |
| Ala (1) | 1.07 |
| Val (1) | 0.99 |
| Met (1) | 1.00 |
| His (2) | 2.00 |
| Pro (3) | 2.88 |

SYNTHESIS EXAMPLE 2

In a manner similar to Synthesis Example 1-(2) described above, 1.1 g of the H-Pro-Val-Met-His(Tos)-Pro-His(Tos)-Gly-Ala-Pro-resin and 1.06 g of Boc-Tyr(Cl$_2$-Bzl)-OH were reacted by double coupling. Then, the removal of the protective groups and the resin was carried out in a manner similar to Synthesis Example 1-(3) described above. The system was similarly purified to obtain 183 mg of H-Tyr-Pro-Val-Met-His-Pro-His-Gly-Ala-Pro-OH (hereafter referred to as "Peptide B").

Rf values: $Rf^1 = 0.04$: $Rf^2 = 0.29$.

Elemental Analysis: (as $C_{51}H_{72}O_{12}N_{14}S \cdot CH_3COOH \cdot 6H_2O$):

|  | C (%) | H (%) | N (%) |
| --- | --- | --- | --- |
| Calcd. | 50.03 | 6.96 | 15.40 |
| Found | 49.68 | 7.07 | 15.92 |

Amino Acid Analysis (analyzed with Hitachi 835 Model):

|  | Analytical Data |
| --- | --- |
| Gly (1) | 1.07 |
| Ala (1) | 1.02 |
| Val (1) | 1.04 |
| Met (1) | 1.02 |
| Tyr (1) | 1.02 |
| His (2) | 2.04 |
| Pro (3) | 2.80 |

Preparation of Antigen

PREPARATION EXAMPLE 1

To 3.0 ml of a 0.05M phosphate buffer (pH=7.0) 5 mg of Peptide A obtained in Synthesis Example 1 and 25 mg of a protein extracted from the ascaris were added and 0.2 ml of a 2% glutaraldehyde solution was dropwise added to the resulting solution. The mixture was stirred at room temperature for 3 hours. Thereafter the reaction mixture was dialyzed at 4° C. against distilled water overnight. After freeze drying, 29 mg of an antigen was obtained. The antigen is hereafter referred to as "Antigen I".

Antigen I bound 10 mols in average of Peptide A per mol of the ascaris (when an average molecular weight was made 100,000). This binding rate of Peptide A to the ascaris was determined as follows: A fraction of Peptide A bound to the ascaris was separated from another fraction of other product (dimer of Peptide A) by gel filtration of Antigen I obtained with Sephadex G-50 (eluting liquid, physiological saline solution; detection, OD 280 nm; eluting rate, 3 ml/hour; fractionated amount, 1 ml each); a calibration curve of a peptide dimer having standard concentrations was prepared to determine the amount of the aforesaid dimer; and the thus determined amount of the dimer was subtracted from the amount of Peptide A used as a raw material, assuming that the thus subtracted amount would be all bound to the ascaris since neither the unreacted ascaris nor Peptide A was recognized. Such is hereafter the same also in the following examples for preparing antigens.

PREPARATION EXAMPLE 2

To 3.0 ml of distilled water 5 mg of Peptide A obtained in Synthesis Example 1 and 25 mg of a protein extracted from the ascaris were added and 200 mg of dicyclohexylcarbodiimide (DCC) was dropwise added to the resulting solution. The mixture was stirred at room temperature for 3 hours. Thereafter the reaction mixture was dialyzed at 4° C. against distilled water overnight. After freeze drying, 28 mg of an antigen was obtained. The antigen is hereafter referred to as "Antigen II".

Antigen II bound thereto 12 mols of Peptide A per mol of the ascaris in average.

PREPARATION EXAMPLE 3

An antigen was obtained in a manner similar to Preparation Example 1 described above except that KLH (Sigma Co., Ltd.) was used instead of the protein extracted from the ascaris. Hereafter the antigen is referred to as "Antigen III". Antigen III bound thereto 10 mols of Peptide A per mol of KLH (when an average molecular weight was made 100,000) in average.

PREPARATION EXAMPLE 4

An antigen was obtained in a manner similar to Preparation Example 2 described above except that KLH (Sigma Co., Ltd.) was used instead of the protein extracted from the ascaris. Hereafter the antigen is referred to as "Antigen IV". Antigen IV bound thereto 9 mols of Peptide A per mol of KLH in average.

PREPARATION EXAMPLE 5

An antigen was obtained in a manner similar to Preparation Example 2 described above except that BSA and Peptide B were used instead of the protein extracted from the ascaris and Peptide A, respectively. Hereafter the antigen is referred to as "Antigen V". Antigen V bound thereto 15 mols of Peptide B per 1 mol of BSA in average.

Preparation of Antibody

PREPARATION EXAMPLE 1

(1) After dissolving 100 μg of Antigen I obtained in Preparation Example (of Antigen) 1 in 1.5 ml of a physiological saline solution, respectively, 1.5 ml of a Freund's adjuvant was added to the solution to obtain a suspension. The suspension was subcutaneously administered to 3 rabbits (2.5 to 3.0 kg). The suspension was given at the same dose 9 times every 2 weeks. After the final administration, blood was collected from the test animals. Antisera (ATLA antibodies of the present invention) were obtained by centrifugation. The antibodies are referred to Antibody I, Antibody II and Antibody III, respectively, to each of the rabbits.

(2) In a manner similar to Preparation Example (of Antibody) 1-(1) above, ATLA antibodies of the present invention were obtained from 6 rabbits (2.5 to 3.0 kg) except that Antigen II obtained in Preparation Example (of Antigen) 2 described above was employed. The antibodies are referred to as Antibody IV, Antibody V, Antibody VI, Antibody VII, Antibody VIII and Antibody IX, respectively, to each of the rabbits.

(3) In a similar manner to Preparation Example (of Antibody) 1-(1) above, ATLA antibodies were obtained except that Antigen III, Antigen IV and Antigen V obtained in Preparation Examples (of Antigen) 3, 4 and 5, respectively, were employed. The thus obtained antibodies are referred to as Antibody X, Antibody XI and Antibody XII, respectively.

(4) Using 500 g of Antigen I prepared in Synthesis Example 1 described above, an antibody was obtained in a manner similar to Preparation Example 1-(1) of Antibody described above. This antibody is referred to as Antibody XIII.

Preparation of Labelled Peptide

PREPARATION EXAMPLE 1

Peptide B obytained in Synthesis Example 2 was labelled in accordance with the method using chloramin T as follows:

That is, 20 μl of a 0.5M phosphate buffer containing 1 mCi of Na ($^{125}$I) (carrier free N.E.N.) was added to 10 μl of a 0.5M phosphate buffer (pH 7.5) containing 5 μg of the aforesaid peptide and then 20 μl of a 0.5M phosphate buffer containing 20 μl of chloramin T was added thereto. After stirring the mixture for 25 seconds at room temperature, 20 μl of a 0.5M phosphate buffer containing 100 μg of sodium metabisulfite ($Na_2S_2O_5$) was added to the mixture to complete the reaction. Then, 10 μl of a cold 10% aqueous sodium iodide solution was added to the reaction mixture. The reaction mixture was passed through a Sephadex G-25 column (1.0 to 50 cm) (eluting liquid, a 0.2M ammonium acetate buffer containing 0.1% BSA and 0.01% $NaN_3$; pH 5.5) to obtain Peptide B labelled with $^{125}$I.

The radioactivity of the thus labelled peptide was 255 μCi/μg.

Measurement of Titer

The titer of each of the antibodies obtained as described above was measured as follows:

That is, each of the antibodies was diluted with a physiological saline solution to 10, $10^2$, $10^3$, $10^4$, $10^5$, . . . times, respectively. To 100 μl each of the thus obtained dilutions, were added 0.1 ml of a $^{125}$I-labelled peptide diluted to about 9500 cpm and 0.2 ml of a 0.05M phosphate buffer (pH=7.4; containing 0.25% BSA, 10mM EDTA and 0.02% $NaN_3$). The mixture was incubated at 4° C. for 24 hours. The resulting antibody-$^{125}$I-labelled antigen complex was separated from the unreacted (unbound) $^{125}$I-labelled peptide by the dextran-activated charcoal method and the centrifugal method (4° C., 30 minutes, 3000 rpm) and the radioactive ray was counted to measure a binding rate (%) of the antibody to the $^{125}$I-labelled peptide at each of the dilution concentrations. The binding rate (%) of the antibody to the $^{125}$I-labelled peptide is taken on the vertical axis and the dilution magnification of the antibody is taken on the abscissa. At each of the concentrations, the binding rate is plotted. Then, the dilution magnification of the antibody where the binding rate shows 50%, i.e., a titer of the antibody, is determined.

The results obtained are shown in Table 1 below.

TABLE 1

| Antibody No. | Titer |
| --- | --- |
| I | 50000 |
| II | 1000 |
| III | 1500 |
| IV | 30000 |
| V | 2500 |
| VI | 20000 |
| VII | 3000 |
| VIII | 15000 |
| IX | 5000 |
| X | 6000 |
| XI | 3000 |

TABLE 1-continued

| Antibody No. | Titer |
| --- | --- |
| XII | 8000 |
| XIII | 6000 |

Test for ATLA Specificity of Antibody (1) Peptide A having various concentrations and ATLA samples described below were employed as samples.

ATLA Positive Sample

To $5 \times 10^9$ of cultured cells of ATLA positive cell line YAM [Science, 217; pp. 737–739 (1982)] 30 ml of a physiological saline solution was added followed by homogenization. Then the mixture was centrifuged (105000×g) for 1 hour to collect the supernatant. The amount of the proteins in the supernatant was adjusted with PBS to 10 mg/ml (the amount of the proteins was measured by a coloration method using a reagent for total protein assay made by the Otsuka Assay Research Laboratories, "Tonein-TP") (hereafter the supernatant is referred to as "YAM Supernatant").

ATLA Negative Sample

Supernatants obtained by treating CCRF-CEM (Immunol. Commun., 9(8), pp. 731–734 (1980)) and BALL-1 (Nature, London, 267, pp. 843–844 (1977)) which were ATLA negative cell lines in a manner similar to above were employed (these supernatants are hereafter referred to as "CEM Supernatant", respectively).

Further, a 0.05M phosphate buffer (pH 7.4) containing 0.25% BSA, 5mM EDTA and 0.02% $NaN_3$ was employed as a standard dilluting solution.

In each of test tubes, 0.2 ml of the standard diluting solution, 0.1 ml of a sample, 0.1 ml of Antibody I obtained in Preparation Example (of Antibody) 1 diluted so as to give a titer of 50,000 in finally obtained assay system and 0.1 ml of $^{125}$I-labelled peptide (a dilution obtained by diluting Labelled Peptide B obtained as described above to about 10000 cpm) were charged. After incubating the mixture at 4° C. for 72 hours, 0.1 ml of normal porcine serum was added thereto. Then, 0.5 ml of a suspension of activated charcoal with dextran was added to the mixture. The mixture was allowed to stand for 30 minutes at 4° C. Thereafter, the mixture was centrifuged at 4° C. for 30 minutes at 3000 rpm to separate the antibody-$^{125}$I-labelled peptide complex (B) from the unreacted (unbound) $^{125}$I-labelled peptide (F). The radioactive ray of the complex was counted to determine a percentage of (B) at each concentration and dilution of the respective samples. The results obtained are shown in FIG. 1 and FIG. 2.

In each of the figures, the vertical axis represents a binding % (B/Bo×100 wherein Bo is a percentage of (B) when the concentration of a sample is made 0) and the abscissa represents concentrations of samples (concentration of Peptide A and, protein contents of YAM Supernatant, CEM Supernatant and BALL Supernatant). In FIG. 1, Curve (a) represents Peptide A. In FIG. 2, Curves (b), (c) and (d) represent YAM Supernatant, CEM Supernatant and BALL Supernatant, respectively.

Figure 2:
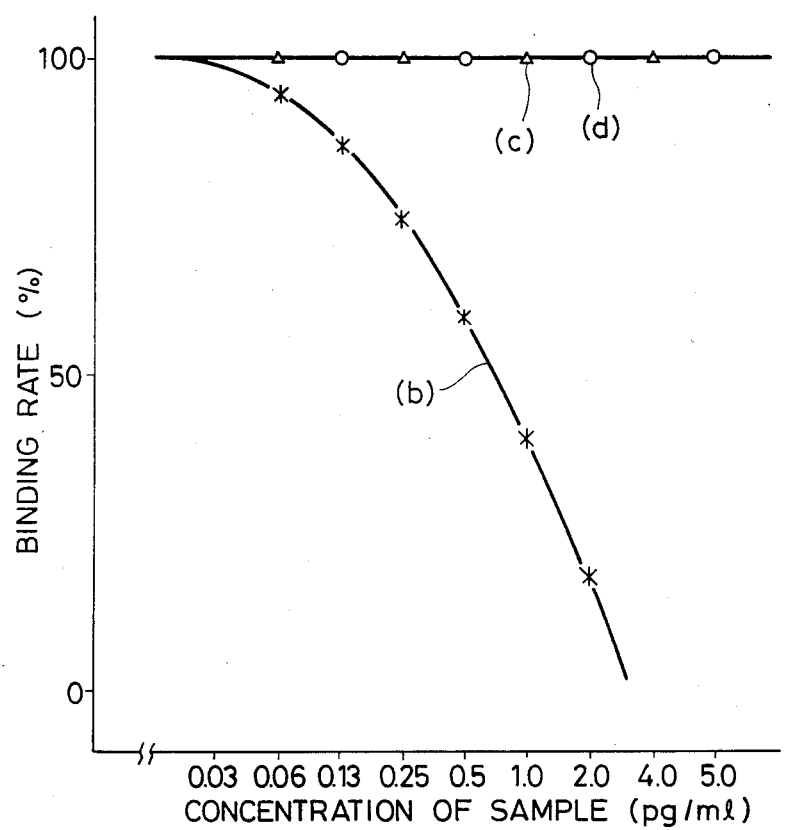
FIG. 2 is a curve showing the reactivity (specificity) of the antibody of the present invention to ATLA.

It is evident that FIG. 1 shows a high degree of the affinity of Antibody I to Peptide A and FIG. 2 shows a high selectivity of the antibody to ATLA. It is further evident from FIG. 2 that no cross reactivity to ATLA negative cell-induced proteins was observed with the antibodies of the present invention.

While the invention has been described in detail and with reference to specific embodiments thereof, it will be apparent to one skilled in the art that various changes and modifications can be made therein without departing from the spirit and scope thereof.

What is claimed is:

1. An antibody to a human leukemia virus-related peptide represented by formula (1):

R-Pro-Val-Met-His-Pro-His-Gly-Ala-Pro-OH  (1)

wherein R is a hydrogen or H-Tyr-; said antibody being isolated from a mammal which has been injected with an antigen which comprises the peptide, as a hapten, covalently bound to a carrier protein via a hapten-carrier coupling agent.

2. The antibody as claimed in claim 1, wherein said carrier protein is selected from the group consisting of an animal serum albumin, an animal serum globulin, an animal thyroglobulin, an animal hemoglobulin, an animal hemocyanin, an ascaris extract, a polylysine, a polyglutamic acid, a lysine-glutamic acid copolymer, and a copolymer containing lysine or ornithine; and said hapten-carrier coupling agent is selected from the group consisting of a diazonium compound, an aliphatic dialdehyde, a dimaleimide compound, a maleimidocarboxyl-N-hydroxysuccinimide ester and a carbodiimide.

3. The antibody as claimed in claim 2, wherein said mammal is rabbit or guinea pig.

4. The antibody as claimed in claim 3, wherein said carrier protein is an ascaris extract, Keyhole limpet hemocyanin or bovine serum albumin and said hapten-carrier coupling agent is glutaraldehyde, N,N-dicyclohexylcarbodiimide or bisdiazotized benzidine.

5. A method for preparing an antibody to a human leukemia virus-associated protein comprising reacting a human leukemia virus-related peptide represented by general formula (1):

R-Pro-Val-Met-His-Pro-His-Gly-Ala-Pro-OH  (1)

wherein R is a hydrogen or H-Tyr-, as a hapten, with a carrier protein in the presence of a hapten-carrier coupling agent to form an antigen, administering the resulting antigen to a mammal to form an antibody, and collecting the antibody.

6. A human leukemia virus-related peptide represented by the general formula (1):

R-Pro-Val-Met-His-Pro-His-Gly-Ala-Pro-OH  (1)

wherein R is a hydrogen or H-Tyr- in which the Tyr moiety may be labelled with radioactive iodine.

7. A peptide according to claim 6, which is represented by the formula

H-Tyr*-Pro-Val-Met-His-Pro-His-Gly-Ala-Pro-OH wherein Tyr* represents Tyr labelled with radioactive iodine.

* * * * *